United States Patent
Defretin et al.

(10) Patent No.: US 6,406,895 B1
(45) Date of Patent: Jun. 18, 2002

(54) PROCESS FOR THE PRODUCTION OF 1,3-PROPANEDIOL BY FERMENTATION

(75) Inventors: Sophie Defretin, Locon; Brigitte Delelis, Vendin les Bethune; Laurent Segueilha, Lambersart, all of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/696,622

(22) Filed: Oct. 25, 2000

(30) Foreign Application Priority Data

Nov. 9, 1999 (FR) .......................................... 99 14072

(51) Int. Cl.[7] .................................................. C12P 7/18
(52) U.S. Cl. ............. 435/158; 435/252.31; 435/252.33; 435/252.7
(58) Field of Search .............................. 435/158, 252.7, 435/252.33, 252.31

(56) References Cited

U.S. PATENT DOCUMENTS 5,593,886 A * 1/1997 Gadddy .................... 435/252.7
5,686,276 A * 11/1997 Laffend et al. ............. 435/158
5,821,092 A * 10/1998 Nagarajan et al. .......... 435/158

FOREIGN PATENT DOCUMENTS

| WO | WO 96/35796 | 11/1996 |
| WO | WO 96/35799 | 11/1996 |
| WO | WO 98/21341 | 5/1998 |
| WO | WO-98/21341 | * 5/1998 |

OTHER PUBLICATIONS

Shen et al., 1990. Appl. Microbiology and Biotechnology, 33: 340–344.*
Webster's Ninth New Collefgiate Dictionary, 1986, Merriam–Webster, Inc. pp. 66 and 495.*
Demain, A.L. and Solomon, N.A., Manual of Industrial Microbiology and Biotechology, American Society for Microbiology, Washington, D.C., pp. 311 and 331.*
Derwent World Patents Index abstract of DE 37 34 764 of May 3, 1999 (Germany).
Derwent World Patents Index abstract of WO 91/15590 of Oct. 17, 1991 (PCT).

* cited by examiner

Primary Examiner—Christoper R. Tate
Assistant Examiner—Kailash C. Srivastava
(74) Attorney, Agent, or Firm—Henderson & Sturm LLP

(57) ABSTRACT

The present invention relates to a process for the production of 1,3-propanediol by the fermentation of a 1,3-propanediol-producing microorganism in a fermentation medium containing glucose, characterized in that the fermentation is carried out without mechanical agitation, with the maintenance of an air retention greater than or equal to 50%, expressed as the volume of gas relative to the total volume of the liquid phase of the fermentation medium, and with the maintenance of a high cell density and a microorganism viability value, determined by a test A, greater than or equal to 95%, preferably of between 95 and 99%, by controlling frothing in the fermentation medium.

7 Claims, No Drawings

PROCESS FOR THE PRODUCTION OF 1,3-PROPANEDIOL BY FERMENTATION

The present invention relates to a process for the production of 1,3-propanediol by the fermentation of a 1,3-propanediol-producing microorganism in a fermentation medium containing glucose.

In particular, the present invention relates to a process for the production of 1,3-propanediol by means of a microorganism which produces 1,3-propanediol from glucose, said process consisting in carrying out the fermentation without mechanical agitation, with the maintenance, in said fermentation medium, of an air retention greater than or equal to 50%, expressed as the volume of gas relative to the total volume of the liquid phase of the fermentation medium, and with the maintenance of a high cell viability of said 1,3-propanediol-producing micro-organisms.

Even more particularly, the present invention relates to a process for the production of 1,3-propanediol wherein the fermentation is carried out in a pneumatic fermenter of the bubble column type, and preferably in a pneumatic fermenter of the bubble column type without gas recirculation, so as to maintain a high gas retention, cell density and cell viability by controlling production of foam in the fermentation medium.

The preparation of 1,3-propanediol by fermentation is normally effected with the aid of microorganisms of the genera Klebsiella, Citrobacter, Clostridium, Lactobacillus, Ilyobacter, Pelobacter or Enterobacter, from glycerol as the carbon source directly assimilable by said microorganism, and under anaerobic fermentation conditions.

In these microorganisms, the metabolic path which leads to the production of 1,3-propanediol from glycerol is based mainly on two successive enzymatic activities belonging to the reductive pathways.

The first enzymatic activity is a glycerol dehydratase, which converts the glycerol to 3-hydroxypropionaldehyde. The second enzymatic activity is an $NADH,H^+$ oxidoreductase, which converts the 3-hydroxypropionaldehyde to 1,3-propanediol.

It is for this reason that specialists in the production of 1,3-propanediol by fermentation acknowledge that, whether it be from glycerol in the case of the natural microorganisms of the genera Kiebsiella, Citrobacter, Clostridium, Lactobacillus, Ilyobacter, Pelobacter or Enterobacter, or whether it be from glucose or other sugars in the case of recombinant microorganisms, said fermentation must preferably be performed under anaerobic conditions because the metabolic pathways for the conversion of glycerol to 1,3-propanediol are not oxidative but reductive pathways.

In fact, the oxidative pathways are only involved in equilibrating the intracellular redox potential—in this case regenerating the cofactor $NADH,H^+$ which is necessary for the conversion of 3-hydroxypropionaldehyde to 1,3-propanediol.

However, patent applications WO 96/35796 and WO 98/21341 describe the cloning of genes coding for these two enzymatic activities and, more particularly, the cloning and expression of at least the glycerol dehydratase activity in specific host cells, for example of the *E. coli* or *S. cerevisiae* type, which are normally fermented under aerobic conditions.

This strategy thus enables 1,3-propanediol to be produced from a less expensive carbon source than glycerol, i.e. mainly from glucose, using only one recombinant microorganism.

Nevertheless, in said patent applications, although said recombinant microorganism containing the gene coding for the dehydratase activity is capable of degrading glucose or other sugars via the pathway for the conversion of glycerol to 1,3-propanediol with a good yield and a good selectivity, the fermentation conditions used are still anaerobic.

In fact, the fermentation conditions described are batch fermentation conditions in mechanically agitated glass serum flasks, i.e. at best microaerobic. Furthermore, these fermentation conditions cannot easily be extrapolated to the industrial scale.

It is apparent from all the above that there is an unsatisfied need for a process which is simple to implement and which makes it possible both to produce said 1,3-propanediol efficiently from a less expensive carbon source than glycerol, i.e. glucose, and also to achieve this result under aerobic conditions.

The Applicant has thus overcome the technical prejudice whereby the fermentation of a 1,3-propanediol-producing microorganism can only be carried out efficiently under anaerobic conditions, by proposing a fermentation process carried out under highly aerobic conditions by using a non-mechanically agitated fermentation under specific conditions, said process furthermore making it possible to maintain a high cell viability of the 1,3-propanediol-producing microorganisms.

In terms of the invention, "highly aerobic conditions" are understood as meaning operating conditions which result in the maintenance, in the fermentation medium, of a high air retention value, i.e. a value greater than or equal to 50%, preferably greater than 70% and particularly preferably greater than or equal to 100%, this percentage being expressed as the volume of gas relative to the total volume of the liquid phase of said fermentation medium.

Also, "non-mechanically agitated fermentation" is understood as meaning a fermentation carried out in pneumatic fermenters of the bubble column type with or without recirculation of the gas used, in contrast to fermenters which contain a mechanical device for agitating the fermentation medium.

Although patent application WO 91/15590 describes a fermentation carried out in a reactor of the bubble column type with gas recirculation, making it possible to produce 1,3-propanediol microbiologically, the microorganism involved here is of the genus Clostridium and the fermentation is carried out on a glycerol basis and under anaerobic conditions.

These anaerobic conditions entail using an oxygen-depleted gas, especially of the nitrogen, argon or carbon dioxide type.

This process is therefore totally unsuitable for the fermentation of 1,3propanediol-producing microorganisms under aerobic conditions.

Anxious to develop a process which would satisfy the practical constraints better than the processes already in existence, the Applicant found that an efficient production of 1,3-propanediol from glucose by means of recombinant micro-organisms could be carried out under highly aerobic conditions in a fermenter of the bubble column type without gas recirculation.

Surprisingly and unexpectedly, the Applicant further found that the high dissolved oxygen content could be maintained in the fermentation medium by controlling production of foam in the fermentation medium, said production of foam being correlatable with the cell population.

The process according to the invention for the production of 1,3-propanediol by the fermentation of a 1,3-propanediol-producing microorganism in a fermentation medium containing glucose is characterized in that the fermentation is carried out without mechanical agitation, with the maintenance of a gas retention greater than or equal to 50%, expressed as the volume of gas relative to the total volume of the liquid phase of the fermentation medium, and with the maintenance of a high cell density and a microorganism viability value, determined by a test A, greater than or equal to 95%, preferably of between 95 and 99%, by controlling production of foam in the fermentation medium.

The 1,3-propanediol-producing microorganism is selected from the group of recombinant microorganisms which are capable of producing 1,3-propanediol from glucose.

The fermentation can be carried out arbitrarily under batch conditions or continuous conditions. It will be advantageous to choose a batch fermentation and particularly preferably a fed batch fermentation, which makes it possible to feed the fermentation medium batchwise with one of the fermentation substrates, in this case glucose, as will be exemplified below.

The Applicant has noticed that 1,3-propanediol production is concomitant with cell growth and also that the total conversion of the glucose used into fermentation products, i.e. on the one hand 1,3-propanediol and on the other hand glycerol and acetic acid as fermentation coproducts, results from the development of a high and viable cell density.

In terms of the invention, "high cell density" is understood as meaning a microorganism population of at least $10^{11}$ cfu/ml of fermentation medium.

For this high cell density value, the viability of the microorganisms must have a value, determined by a test A, greater than or equal to 95%, preferably of between 95 and 99%.

To measure the cell viability, the Applicant recommends determining the physiological state of the microorganism population by means of the technique of flux cytometry.

This technique is capable of analyzing several cell characteristics individually and at high speed (10,000 cells/second), making it possible e.g. simultaneously to differentiate the viable microorganisms from the non-viable microorganisms in a given cell population and to count them accurately.

Said count is effected by using a flux cytometer, such as the CHEM FLOW® Autosystem with laser detection, developed by CHEMUNEX, to measure the fluorescence emitted by the microorganisms labelled beforehand with specific fluorochromes.

The method comprises three phases. The first consists in labelling the viable microorganisms by causing them to assimilate a non-fluorescent substrate capable of passing through their cell membrane. This non-fluorescent substrate is then hydrolyzed by the esterases in their cytoplasm to give a compound which, when excited by a laser, emits a green and red fluorescence. Only the viable cells are labelled in this way.

The second phase consists in labelling the non-viable microorganisms by means of a DNA-specific reagent which emits a red fluorescence when excited by the laser.

Finally, the third phase consists in analyzing the cell suspension in the analyzer of the CHEM FLOW® Autosystem flux cytometer.

The labelled microorganisms emit the fluorescent signal, which is analyzed in the green and red with the aid of two very sensitive detectors. Thus the total number of microorganisms (viable and non-viable) will be determined in the red, while the number of viable microorganisms will be determined from the green fluorescent signal.

Therefore, after the preparation of a homogeneous cell suspension containing in the order of $5.10^6$ cfu/ml from the fermentation medium by successive dilutions with the reagent ChemSol B7marketed by CHEMUNEX, the test A consists in performing the following steps:

For the "viability" marker:
100 μl of the homogenized cell suspension are placed in a 3 ml tube together with 900 μl of the viability marker solution marketed by CHEMUNEX,
the mixture is homogenized and the tubes are incubated for 10 min at 30° C., and
the tubes are placed in ice in the dark to stop the reaction.

For the "mortality" marker:
100 μl of the homogenized cell suspension are placed in a 3 ml tube together with 900 μl of the mortality marker solution marketed by CHEMUNEX,
the mixture is homogenized and the tubes are incubated for 10 min in ice in the dark.

Measurements are then made on a ChemFlow® Autosystem 3 in the following manner (after calibration with the aid of a standard specially developed for the analysis of bacterial suspensions):
150 μl of the suspension labelled with the viability marker are mixed with 150 μl of the suspension labelled with the mortality marker, and
1.2 ml of the reagent ChemSol B7are added, the measurement being made on 225 μl.

The measuring instrument provides a total count (TC) value corresponding to the total number of events counted during the analysis, and a GC value corresponding to the number of living cells.

The percentage viability will be determined by the ratio (GC/TC)×100.

The Applicant has also shown that the best development of the 1,3-propanediol-producing recombinant microorganism is correlated with the transfer of oxygen from the nutrient medium into the cell, only the dissolved oxygen being assimilated by the cell.

Now, it is known quite generally to those skilled in the art that, to ensure this oxygen transfer, it is necessary to have adequate agitation and aeration means.

It has been established by the Applicant that, to assure an effective oxygen transfer for these recombinant microorganisms which produce 1,3-propanediol from glucose under aerobic conditions, said oxygen transfer must reach a value greater than 3 g/l/h, expressed in grams of oxygen per litre of fermentation medium per hour.

In this case, the solution normally recommended by those skilled in the art is to work with a supply of pure oxygen, or to apply a counterpressure of air so as to increase the dissolved oxygen content of the medium, or to carry out the fermentation with vigorous mechanical agitation.

However, the energy cost of such an oxygen transfer is too prohibitive and this technique results in a high degree of cell lysis due to mechanical stress.

Furthermore, the Applicant has also established that, in the case of a fermentation with such a dissolved oxygen demand, i.e. requiring an oxygen transfer greater than or equal to 3 g/l/h, the industrial feasibility of a fermenter in which the fermentation medium is agitated mechanically is not conceivable, given the useful volumes of more than 100 m³ which may be involved.

Consequently, and according to the present invention, the fermentation is carried out without mechanical agitation by using pneumatic fermenters of the bubble column type, and preferably a pneumatic fermenter of the bubble column type without air recirculation.

It is quite generally advisable to use a pneumatic fermenter of the bubble column type for obtaining an oxygen transfer greater than that of a fermenter in which the fermentation medium is agitated mechanically, at an equivalent energy cost.

However, the aeration rates necessary to achieve an oxygen transfer greater than 3 g/l/h require linear gas velocities in excess of 5 cm/s, which cause a high degree of cell lysis and hence considerable production of foam.

Surprisingly and unexpectedly, the Applicant has shown that the amount of dissolved oxygen required in the fermentation medium in order to assure an effective production of 1,3-propanediol by said recombinant microorganisms can be supplied by specifically controlling production of foam in the fermentation medium.

It is advantageously chosen to maintain a high air retention and to maintain a high cell viability of the microorganisms in the fermentation medium by promoting production of foam in said fermentation medium.

It is also chosen preferentially to control the gas retention in the fermentation medium by supplying a large amount of air, and to limit the antifoam supply, as will be exemplified below, rather than to adopt the commonly acknowledged procedure of managing the fermentation by eliminating production of foam in the fermentation medium.

Production of foam in the fermentation medium is promoted by applying a technique chosen from the group consisting of control of the antifoam supply and/or addition of a surfactant. It is preferably chosen to control the antifoam supply.

However, it can also be chosen to use surfactants in order to promote production of foam in combination with a high air flow rate.

Other characteristics and advantages of the invention will become apparent from the following Example, which is given only by way of illustration and without implying a limitation.

EXAMPLE

A growth medium consisting of 10 g/l of yeast extract, 16 g/l of tryptone and 5 g/l of NaCl is inoculated at a rate of 0.2% with a recombinant *E. coli* which produces 1,3-propanediol from glucose under the conditions described in patent application WO 96/35796.

This preculture is incubated at 35° C. for 4 hours to give a cell density representing an absorbance of 1 unit of OD at 550 nm.

A fermentation medium which has the same composition as the preculture medium but additionally contains 10 g/l of glucose is inoculated at a rate of 10% with said preculture and introduced into a pneumatic fermenter of the bubble column type without air recirculation, said fermenter having a useful volume of 20 l.

A glucose solution with a concentration of 50% by dry weight is fed batchwise into this medium so as to keep the glucose concentration at a value of at most 10 g/l.

Similarly, as recommended in patent application WO 96/35796, vitamin B12 is added at a rate of 1.2 mg/h.

Incubation is carried out at 35° C., the pH of the fermentation medium being regulated at a value of 6.8 by adding 20% $NH_4OH$.

The air feed velocity is 5.4 cm/s for a liquid volume of 6 l. The expanded volume, consisting of the volume of liquid plus the volume of air, is 12 l, resulting in a gas retention of 100%. The resulting oxygen transfer rate is established at 3 g/l/h. The cell viability, determined by the test A, is thus 97% for a population of $2.10^{10}$ cfu/ml.

The supply of EROL 18 antifoams, marketed by OUVRIE, is limited to a value of 1‰.

When the fermentation is complete (i.e. when all the glucose introduced has been consumed), 70 g/l of 1,3-propanediol have been produced concomitantly with 25 g/l of glycerol and 8 g/l of acetic acid.

This fermentation procedure allows an oxygen transfer of 3 g/l/h, whereas under conventional conditions it would have been 1.5 g/l/h with an oxygen retention of 40%.

The process is therefore particularly suitable for the efficient production of 1,3-propanediol by these aerobic recombinant strains.

What is claimed is:

1. Process for the production of 1,3-propanediol by the fermentation of a 1,3-propanediol-producing microorganism in a fermentation medium containing glucose, under aerobic conditions, wherein the fermentation is carried out without mechanical agitation and with an air retention greater than or equal to 50%, expressed as the volume of gas relative to the total volume of the liquid phase of the fermentation medium, a microorganism population of at least $10^{11}$ cfu/ml of fermentation medium, and a microorganism viability value, determined by the technique of flux cytometry, greater than or equal to 95%, and wherein in said process, the production of foam is promoted by limiting the antifoam supply.

2. Process according to claim 1, wherein the microorganism viability value is between 95 and 99%.

3. Process according to claim 1, wherein the fermentation without mechanical agitation is carried out in a fermenter selected from the group consisting of pneumatic fermenters of a bubble column type.

4. Process according to claim 3, wherein the fermentation is carried out in a pneumatic fermenter of a bubble column type without-air recirculation.

5. Process according to claim 1, wherein production of foam is promoted in the fermentation medium by applying a technique selected from the group consisting of limiting the antifoam supply to a value of 1‰, and/or addition of a surfactant.

6. Process according to claim 1, wherein the fermentation is carried out so as to maintain the air retention in the fermentation medium at a value greater than 70%, expressed as the volume of air relative to the total volume of the liquid phase of the fermentation medium.

7. Process according to claim 1, wherein the air retention in the fermentation medium is maintained at a value greater than or equal to 100%, expressed as the volume of air relative to the total volume of the liquid phase of the fermentation medium.

* * * * *